United States Patent [19]
Akbik

[11] Patent Number: 6,086,553
[45] Date of Patent: Jul. 11, 2000

[54] ARTERIOVENOUS SHUNT

[76] Inventor: Mohamad J. Akbik, #920 Madison S. 825, Memphis, Tenn. 38103

[21] Appl. No.: 09/345,413

[22] Filed: Jul. 1, 1999

[51] Int. Cl.⁷ .................................................... A61M 5/00
[52] U.S. Cl. .............................................. 604/8; 604/175
[58] Field of Search .................................. 604/8, 9, 175, 604/164

[56] References Cited

U.S. PATENT DOCUMENTS

| | | | |
|---|---|---|---|
| 3,638,649 | 2/1972 | Ersek . | |
| 3,713,441 | 1/1973 | Thomas . | |
| 3,818,511 | 6/1974 | Goldberg et al. . | |
| 3,826,257 | 7/1974 | Buselmeier | 604/8 |
| 3,853,126 | 12/1974 | Schulte . | |
| 3,998,222 | 12/1976 | Shihata | 604/8 |
| 4,479,798 | 10/1984 | Parks . | |
| 4,822,341 | 4/1989 | Colone | 604/175 |

*Primary Examiner*—Mark O. Polutta
*Assistant Examiner*—Kelly M Cheney
*Attorney, Agent, or Firm*—Jacobson, Price, Holman & Stern, PLLC

[57] ABSTRACT

A vascular access that can be used for hemodialysis and other conditions where a vascular access may be needed. A soft main tube made of PTFE is used with two extension tubes. The ends of the main tube are anastomosed to an artery and a vein. The extension tubes connected to the main tube at one end are connected to the dialysis machine at an opposite end. The entire graft (main tube) is placed in the subcutaneous or deep tissues except for the two exposed ends of the extension tubes which remain in the external position allowing an easy, non-traumatic access to the blood flow.

16 Claims, 1 Drawing Sheet

ARTERIOVENOUS SHUNT

FIELD OF THE INVENTION

The present invention relates to the surgical joining of an artery and a vein under the skin by a main shunt tube having two extension tubes used for the purpose of hemodialysis.

BACKGROUND OF THE INVENTION

More than 800,000 patients worldwide suffer from chronic renal failure. Renal failure is most often the result of inflammatory diseases of the kidney, leading to a continuous decline of the kidney function until the kidneys are no longer able to keep the levels of certain toxic substances in the blood at low levels. Also those suffering from diabetes and chronic abusers of pain relief drugs may experience chronic renal failure.

Hemodialysis is a widely used treatment modality for individuals whose kidneys are unable to remove undesirable products from their system, due to acute or chronic reasons. When the damage is irreversible and the kidneys cannot recover their proper functions, the person is in a state of end stage renal disease (ESRD).

To maintain one's state of health there are three treatment modalities available, those being:1. renal transplant, 2. peritoneal dialysis, and 3. chronic hemodialysis. Even though the first two modalities are often used, chronic hemodialysis is by far the most widely used treatment.

In order to provide this treatment, a vascular access is used as part of a system of allowing the blood to be circulated extracorporaly in a dialysis machine and then to re-enter the body. The most widely used methods of vascular access are:1. a direct arteriovenous anastomosis (Cimino type), 2. a large bore external venous catheter, or 3. a tube planted subcutaneously and anastomosing one end to an artery and one end to a vein (arteriovenous (AV) graft).

For a variety of reasons, the AV graft is the most widely used at the present time. Typically the graft is planted subcutaneously in an extremity with one end anastomosed to the artery and the other end anastomosed to the vein. This allows the blood to circulate at a high velocity in the graft.

When the graft is matured (ready to be used) it is accessed by inserting a large bore needle in the arterial side. The blood then comes out from the arterial needle and enters via an external tubing system into the dialysis machine. After the blood is dialyzed, it re-enters the graft via the venous side.

This method is very effective but because of the need to repeatedly cannulate the graft by introducing a sharp needle, there is a high rate of complications. These complications and problems include a great deal of discomfort for the patient, loss of function of the graft and a financial drain. These complications, most of which are caused by repeated cannulation of the graft, include infection, thrombosis, false aneurysm, bleeding, skin necrosis, skin sloughing and also pain and discomfort to the patient each time they have dialysis.

SUMMARY OF THE INVENTION

The arteriovenous shunt of the present invention includes a smooth main graft tube made of polytetrafluoroethylene (PTFE), having a length of 8 to 13 cm with a lumen diameter of 4 to 6 mm. One end of the main tube is anastomosed to a peripheral artery and the other end of the main tube is anastomosed to a peripheral vein. Connections between the main tube and blood vessels is made by anastomosing (suturing) the end of the main tube to the side of the vein. This can be done in the person's limb or any other suitable vein and artery.

At a specific distance of 3 to 5 cm from the attached ends of the main tube, two extension tubes are attached to the main tube. The two extension tubes are made of a suitable material, such as PTFE, and have a length of 3 to 5 cm and a lumen diameter of 2 to 3 mm.

PTFE provides a superior product in so far that it is more adaptable to the anatomical location where shunts are placed. It allows a formation of a fibrous capsule which will reduce rejection or infections. Blood is less likely to clot in a PTFE graft.

Because of the diameter of the lumens of the two extension tubes, a 2 to 3 mm angioplasty catheter can be introduced via the venous port to dilate stenosis at the venous anastomotic site and in the vein itself, which avoids the prior problems of clotting of shunts and resultant slow blood flow in the shunt. Reduced blood flow prevents adequate dialysis. Also, a catheter can be introduced via the arterial port and advanced to various arteries to perform diagnostic and therapeutic studies without puncturing an artery which can by itself cause a variety of complications.

At a point located 3 to 5 cm from the arterial anastomosis one extension tube is connected to the main tube (using a sealant and/or anastomosis). The opposite end of this extension tube is brought through a subcutaneous tunnel outside the skin and is attached to a hemostatic valve, or another means to control blood flow. A cuff producing intense fibrosis can be placed around this extension tube at the point of exit through the skin.

Another similar extension tube is attached in a similar way to the main tube and is brought outside the body through a common point as the arterial extension tube in a similar way and attached to a hemostatic valve. This extension tube is the venous extension tube.

The distance between the connections of the extension tubes and the main tube must be between 2 and 3 cm to avoid recirculation of dialyzed blood back to the dialysis machine and to avoid extensive vibrations as blood reenters the main tube, which can lead to damage of blood vessels. This separation distance will give enough distance for the dialyzed blood to join the venous circulation. The extension tubes should be close enough so that they can be joined externally and exit through one port, thus reducing exposure points of the patient and the risk of infections.

The arteriovenous shunt can be placed in several anatomical locations where peripheral veins and arteries of sufficient blood flow are in close proximity so that the two ends of the main tube can be attached to both vein and artery without difficulty. The "shunt" placement is preferably in the distal part of either one of the upper extremities.

The device can be placed in a subcutaneous plane or in a deep tissue plane. Placing the shunt in a deep tissue plane is preferable since cannulations of the shunt are not needed. Thus a location close to the surface is not required. Deeper tissue locations will decrease the likelihood of external injury and infection.

After appropriate preparations and under sterile conditions, with proper anesthesia, a small incision is made in the anticubital area. Through this incision the brachial artery and a vein of adequate lumen, usually the cephalic vein, are isolated. A segment of adequate length of both artery and vein is prepared for anastomosis.

At a point 5 to 7 cm distal to the anticubital incision, another small incision is made. With blunt dissection, a U-shaped tunnel is developed between the two incisions. The venous part of the graft main tube is brought through the lateral part of the U-shaped tunnel, from the distal incision to the anticubital incision to meet the vein. The arterial part of the graft main tube is brought in similar fashion through the medial part of the U-shaped tunnel to meet the artery. There will be a distance of 3 to 4 cm between the curved end of the U-shaped tunnel and the distal incision. This will allow most of the arterial and venous extensions to be buried subcutaneously and only a short segment of the tube extensions will be exposed.

Once the two ends of the graft main tube are located properly to meet the vein and the artery, the anastomosis is performed between the venous end of the graft main tube and the side of the vein. Upon completion, a heparinized solution is installed in the graft main tube via the arterial end to test the anastomosis. When the integrity of the anastomosis is established, the soft vascular clamps, which were previously placed on the vein distal and proximal to the anastomosis site, are removed and a vascular clamp is placed on the graft main tube just distal to the venous anastomosis.

The anastomosis between the artery and the graft is done in a similar fashion. Before completing this anastomosis the blood is allowed to flow from the venous side to flush any air that is present in the graft main tube and then the arterial anastomosis is completed. Once arterial anastomosis is completed, a heparinized solution is placed into the graft main tube via the arterial and venous extension tubes using their hemostatic valves. At this point both valves are kept securely tightened.

The clamps are removed from the artery proximal and distal to the arterial anastomosis and flow in the graft main tube is established. At this point, further flushing of the graft main tube through hemostatic valves can be done making sure that an adequate amount of heparinized solution remains in the arterial and venous extension tubes. After good homeostasis is accomplished, the anticubital incision is appropriately closed. Also, several sutures might be needed to close the distal incisions. One or two heavy silk stitches are used to secure the extensions to the skin at the single exit port.

As the extension tubes exit the skin they will be surrounded with antimicrobial and tissue ingrowth cuffs which remain in subcutaneous locations. This will prevent migration of bacteria and enhance fibrosis around the tubes.

The extension "access" tubes are made of silastic material and can be connected to the main tube by using a biological sealant. In the device, the connection/extension "access" tubes exit the skin from one site. As the connection/extension tubes exit the skin they lie parallel to the skin and can be concealed easily by a light bandage or dressing. The tips of the extension tube can be manipulated at the time of dialysis so they can be easily accessed.

In this way, the entire graft of the main tube and most of the arterial and venous extension tubes are placed subcutaneously or even in a deep tissue plane, since direct cannulation of the graft is not needed. Only the tips of the arterial and venous extension tubes, including hemostatic valves, or another means to control blood flow, are located outside the skin.

The arteriovenous shunt can be used within 24 to 48 hours after insertion. A connection or cannulation is established between the arterial extension tube valve and an external tube that will take blood to the dialysis machine by release of a blood flow control mechanism. The blood will return from the dialysis machine via an external tube to the venous extension tube hemostatic valve and back through to the venous circulation.

During hemodialysis, patient's blood flows through an extracorporeal circuit, consisting of the dialyzer, the blood lines, and the hemodialysis machine. The machine provides and controls the constant flow of blood. Inside the dialyzer, blood passes the inner lumen of thousands of capillary membranes. Uremic toxins accumulated in the patient's blood diffuse through the membrane while blood cells and proteins are retained. Outside the membranes a constant flow of dialysate (an aqueous solution containing physiologic salts) removes these uremic toxins. At the same time, water is extracted from patient's blood by ultrafiltration, and purified blood is chanelled into the blood circulation again.

The present invention may also be used for arterial monitoring and blood can be drawn for arterial testing. It can also be used for chronic and acute venous access.

This device eliminates the need to cannulate the graft of the main tube by the use of sharp needles and allows the blood to flow at a high velocity. This device provides following advantages 1. eliminates the pain and discomfort resulting from repeated sharp needle cannulations, 2. significantly reduces the risk of graft infection, 3. eliminates hematomas, graft wall weakness and false aneurysms, 4. eliminates damage to the grafts' newintema, thus increasing the patency of the graft, and finally 5. eliminates the need to apply pressure on the graft and decreases the incidence of clotting.

The device of the present invention provides an arteriovenous vascular access and can be utilized easily by minimally trained professionals. It will be well tolerated by patients and can be used for chronic and/or acute hemodialysis. By allowing a high velocity blood flow, the time needed for dialysis is reduced, with less rate of infection and thrombosis, and other complications and allows uninterrupted treatment with a longer patency rate.

The device is easy to utilize and requires minimal nursing skills. It is safe to use due to the hemostatic valves that will control flow of blood. In case of thrombosis, thrombocytic agents can be instilled in the graft main tube with ease.

When stenosis occurs at the venous anastomosis site due to intimal hyperplasia angioplasty, dilatation of the site can be done easily by introducing an angioplasty catheter via the venous extension tube and advancing it under fluoroscopy guidance to the site of the stenosis which then can be dilated. The catheter will then be withdrawn and flow reestablished.

Accordingly, it is an object of the present invention to provide an arteriovenous shunt anastomosed to a vein and an artery and having two extension tubes connected thereto leading exteriorly for connection with a dialysis machine.

It is another object of the present invention to provide an arteriovenous shunt anastomosed to a vein and an artery and having two extension tubes connected thereto leading exteriorly for connection with a dialysis machine with the main shunt tube having an overall length of 7 to 13 cm with the separation distance between the two extension tubes being 2 to 3 cm so as to avoid recirculation of dialyzed blood back to the dialysis machine.

It is still yet another object of the present invention to provide an arteriovenous shunt anastomosed to a vein and an artery and having two extension tubes connected thereto leading exteriorly for connection with a dialysis machine with the main shunt tube having an overall length of 7 to 13 cm with the separation distance between the two extension tubes being 2 to 3 cm so as to avoid recirculation of dialyzed blood back to the dialysis machine and with the main shunt tube having a lumen of 4 to 6 mm and the two extension tubes having a lumen of 2 to 3 mm.

It is still yet another further object of the present invention to provide an arteriovenous shunt anastomosed to a vein and an artery and having two extension tubes connected thereto leading exteriorly for connection with a dialysis machine with the main shunt tube having an overall length of 7 to 13 cm with the separation distance between the two extension tubes being 2 to 3 cm so as to avoid recirculation of dialyzed blood back to the dialysis machine and with the main shunt tube having a lumen of 4 to 6 mm and the two extension tubes having a lumen of 2 to 3 mm so as to gain access for diagnostic and therapeutic uses.

These and other objects of the invention, as well as many of the intended advantages thereof, will become more readily apparent when reference is made to the following description taken in conjunction with the accompanying drawings.

BRIEF DESCRIPTION OF THE DRAWING

The FIGURE is a schematic representation of an arteriovenous shunt including a main tube graft anastomosed to an artery and a vein with two extension tubes leading out from under the skin of a patient.

DETAILED DESCRIPTION OF THE PREFERRED EMBODIMENTS

Figure 1:
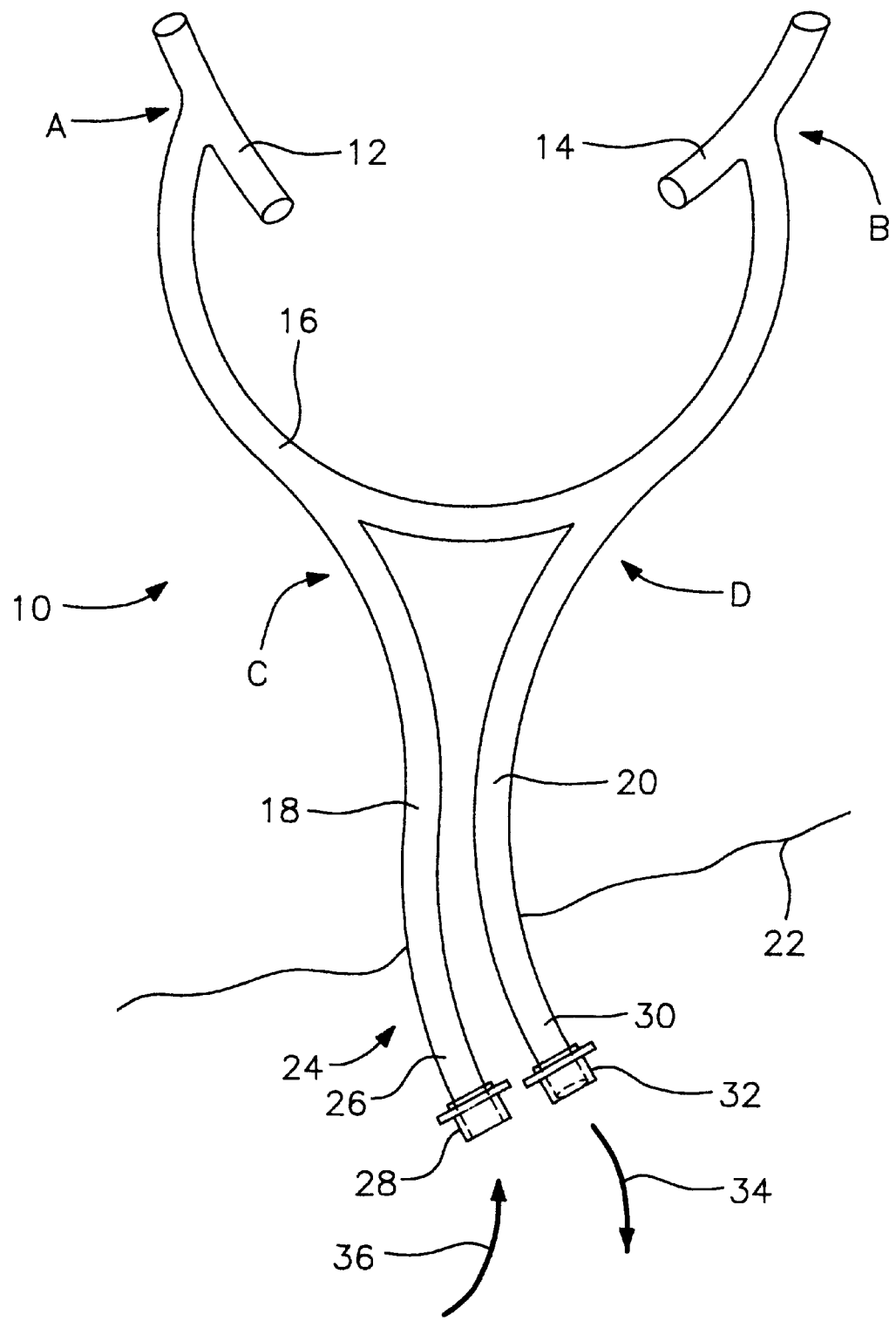

In describing a preferred embodiment of the invention illustrated in the drawings, specific terminology will be resorted to for the sake of clarity. However, the invention is not intended to be limited to the specific terms so selected, and it is to be understood that each specific term includes all technical equivalents which operate in a similar manner to accomplish a similar purpose.

With reference to the drawing, in general an arteriovenous shunt embodying the teachings of the subject invention is generally designated as 10. With reference to its orientation in the FIGURE, a peripheral vein 12 and a peripheral artery 14 are schematically shown. Interconnecting the vein 12 and artery 14 is a main tube 16. Main tube 16 has a length from connection point A at the vein to connection point B at the artery has a length of 7 to 13 cm.

Connected to the main tube 16 are two extension tubes 18 and 20. Extension tube 18 connected to tube 16 at point C has a length of 3 to 5 cm. The separation distance between points A and C is 3 to 5 cm. Similarly, extension tube 20 is connected to main tube 16 at point D. The separation distance between points B and D is approximately 3 to 5 cm. The separation distance between extension tubes 18 and 20 along the main tube 16, as represented by points C and D, is approximately 2 to 3 cm.

Extension tubes 18 and 20 form a venous extension and an artery extension, respectively. The two extension tubes 18, 20 extend substantially parallel and adjacent to each other over a majority of their respective lengths so as to pass through the skin 22 of a patient in close proximity and thereby exit through a single outlet port generally designated 24.

At the terminal end 26 of extension tube 18 is located a hemostatic valve 28. Similarly, at the terminal end 30 of extension tube 20 is located a hemostatic valve 32.

During use, the arteriovenous shunt 10 is connected with a dialysis machine such that blood flows in the direction of arrow 34 from peripheral artery 14 and into the dialysis machine. Upon cleansing of the blood, the return flow of blood moves in the direction of arrow 36 to return blood to the peripheral vein 12.

The foregoing description should be considered as illustrative only of the principles of the invention. Since numerous modifications and changes will readily occur to those skilled in the art, it is not desired to limit the invention to the exact construction and operation shown and described, and, accordingly, all suitable modifications and equivalents may be resorted to, falling within the scope of the invention.

I claim:

1. An arteriovenous shunt for surgical implantation comprising:

a main tube having two ends for subcutaneous implantation and respective connection to a side of a peripheral artery and a side of a peripheral vein, two extension tubes, each of said two extension tubes having two ends with one end of said two extension tubes being subcutaneously connected to said main tube and an opposite free end of said two extension tubes terminating in a hemostatic valve for connection to an input and an output, respectively, of a dialysis machine, said two extension tubes extending substantially parallel and adjacent to each other from said free end towards said one end of said two extension tubes over a majority of their respective lengths so as to exit from the skin of a patient through a single outlet port, and a separation distance between said one end of each of said two extension tubes subcutaneously connected to said main tube being sufficient for dialyzed blood to join venous circulation while avoiding recirculation of the dialyzed blood back to the dialysis machine and close enough so that said two extension tubes exit through said single outlet port to reduce exposure of the patient to a risk of infection.

2. An arteriovenous shunt for surgical implantation as claimed in claim 1, wherein the main tube has a length of 8 to 13 cm.

3. An arteriovenous shunt for surgical implantation as claimed in claim 2, wherein the extension tubes have a length of 3 to 5 cm.

4. An arteriovenous shunt for surgical implantation as claimed in claim 1, wherein the two extension tubes are connected to the main tube with said separation distance of 2 to 3 cm.

5. An arteriovenous shunt for surgical implantation as claimed in claim 4, wherein one of the extension tubes is connected to the main tube at a distance of 3 to 5 cm from one end of the main tube.

6. An arteriovenous shunt for surgical implantation as claimed in claim 5, wherein the other of the extension tubes is connected to the main tube at a distance of 3 to 5 cm from the other end of the main tube.

7. An arteriovenous shunt for surgical implantation as claimed in claim 1, wherein the main tube has a lumen of 4 to 6 mm and the two extension tubes have a lumen of 2 to 3 mm.

8. An arteriovenous shunt for surgical implantation as claimed in claim 1, wherein the main tube and the extension tubes are made of polytetrafluoroethylene.

9. An arteriovenous shunt for surgical implantation comprising:

a main tube having two ends for subcutaneous implantation and respective connection to a side of a peripheral artery and a side of a peripheral vein, two extension tubes, each of said two extension tubes having two ends with one end of said two extension tubes being subcutaneously connected to said main tube, said two extension tubes extending substantially parallel and adjacent to each other over a majority of their respective lengths so as to exit from the skin of a patient through a single outlet port, and a separation distance between said one end of each of said two extension tubes subcutaneously connected to said main tube being sufficient for dialyzed blood to join venous circulation while avoiding recirculation of the dialyzed blood back to the dialysis machine and close enough so that said two extension tubes exit through said single outlet port to reduce exposure of the patient to a risk of infection.

10. An arteriovenous shunt for surgical implantation as claimed in claim 9, wherein the main tube has a length of 8 to 13 cm.

11. An arteriovenous shunt for surgical implantation as claimed in claim 10, wherein the extension tubes have a length of 3 to 5 cm.

12. An arteriovenous shunt for surgical implantation as claimed in claim 9, wherein the two extension tubes are connected to the main tube with said separation distance of 2 to 3 cm.

13. An arteriovenous shunt for surgical implantation as claimed in claim 12, wherein one of the extension tubes is connected to the main tube at a distance of 3 to 5 cm from one end of the main tube.

14. An arteriovenous shunt for surgical implantation as claimed in claim 13, wherein the other of the extension tubes is connected to the main tube at a distance of 3 to 5 cm from the other end of the main tube.

15. An arteriovenous shunt for surgical implantation as claimed in claim 9, wherein the main tube has a lumen of 4 to 6 mm and the two extension tubes have a lumen of 2 to 3 mm.

16. An arteriovenous shunt for surgical implantation as claimed in claim 9, wherein the main tube and the extension tubes are made of polytetrafluoroethylene.

* * * * *